United States Patent
Yanagawa et al.

(10) Patent No.: US 7,205,445 B2
(45) Date of Patent: Apr. 17, 2007

(54) METHOD OF CONTINUOUS PRODUCTION OF POLYALKYLBIPHENYLS

(75) Inventors: Shinichiro Yanagawa, Yokohama (JP); Shouzou Hayashi, Yokohama (JP)

(73) Assignee: Nippon Petrochemicals, Co., Ltd., Tokyo (JP)

( * ) Notice: Subject to any disclaimer, the term of this patent is extended or adjusted under 35 U.S.C. 154(b) by 508 days.

(21) Appl. No.: 10/647,592

(22) Filed: Aug. 26, 2003

(65) Prior Publication Data
US 2004/0073074 A1   Apr. 15, 2004

(30) Foreign Application Priority Data
Aug. 30, 2002   (JP) .............................. 2002-255402

(51) Int. Cl.
*C07C 2/00* (2006.01)
*C07C 6/00* (2006.01)

(52) U.S. Cl. ...................... 585/422; 585/464; 585/467; 585/716

(58) Field of Classification Search ............... 585/422, 585/464, 467, 716
See application file for complete search history.

(56) References Cited

U.S. PATENT DOCUMENTS

| 4,783,567 A | * | 11/1988 | Kocal | 585/464 |
| 4,982,037 A | * | 1/1991 | Nakamura et al. | 585/467 |
| 5,817,908 A | * | 10/1998 | Mehlberg | 585/716 |

FOREIGN PATENT DOCUMENTS

| EP | 0285280 A1 | * | 10/1988 |
| EP | 0508835 A2 | * | 10/1992 |
| JP | 49-80045 | | 8/1974 |
| JP | 56-156222 | | 12/1981 |
| JP | 03-106833 | | 5/1991 |
| JP | 09-040588 | | 2/1997 |

* cited by examiner

*Primary Examiner*—Walter D. Griffin
*Assistant Examiner*—Prem C. Singh
(74) *Attorney, Agent, or Firm*—Dickstein Shapiro LLP

(57) ABSTRACT

A method of continuously producing polyalkylbiphenyls involves reacting biphenyl and an olefin in the presence of a solid acid catalyst to obtain a reaction mixture containing monoalkylbiphenyls and dialkylbiphenyls, separating a fraction containing biphenyl and at least a part of the monoalkylbiphenyls, circulating the separated fraction to the reactor such that the ratio of biphenyls to monoalkylbiphenyls is designed to be 0.1 or more and is designed to be less than the soluability of biphenyl to monoalkylbiphenyl at a circulation temperature, and recovering polyalkylbiphenyls.

4 Claims, 1 Drawing Sheet

1: Raw material supply line
2: Reactor
3: Reaction mixture transfer line
4: Distillation tower
5: Circulation line
6: Recovery line 1: Raw material supply line
2: Reactor
3: Reaction mixture transfer line
4: Distillation tower
5: Circulation line
6: Recovery line

METHOD OF CONTINUOUS PRODUCTION OF POLYALKYLBIPHENYLS

BACKGROUND OF THE INVENTION

1. Field of the Invention

The present invention relates to a method of continuously producing an alkylbiphenyl useful as a functional fluid such as a pressure-sensitive paper solvent, heating medium and insulating oil.

2. Description of the Related Art

Alkylbiphenyls are used as a pressure-sensitive paper solvent, heating medium, insulating oil and various solvents and various studies have been made as to a method of producing them.

There is described a method of reacting biphenyl and propylene in the presence of an aluminum chloride catalyst in the publication of Japanese Patent Application Laid-Open (JP-A) No. 49-80045. However, in the case of using a catalyst such as aluminum chloride, a water-washing and neutralizing step is required after the reaction, the step causing the generation of a large amount of waster water. Also, the equipment to be used must be constructed of acid-resistant materials. Accordingly, it is difficult to run a continuous reaction and produce alkylbiphenyls efficiently.

In the publication of JP-A No. 56-156222, there is described a method of alkylating biphenyl by using an olefin in the presence of a silica-alumina catalyst or zeolite catalyst. However, only a method is disclosed in which monoalkylbiphenyls rich in m- and p-position substituted bodies is produced in a batch system and it is therefore difficult to produce polyalkylbiphenyls such as dialkylbiphenyls and trialkylbiphenyls in a large amount efficiently.

In the publication of JP-A No. 9-40588, there is a method of producing a p-isopropylbiphenyl in a continuous flow system comprising a step of running an isomerization reaction of a m-isopropylbiphenyl and biphenyl, a step of separating a p-isopropylbiphenyl and a circulation step of returning the remainder product from which the p-isopropylbiphenyl has been separated. However, there is no description concerning a method of producing polyalkylbiphenyls such as dialkylbiphenyls and trialkylbiphenyls by using biphenyl and an olefin as starting materials.

Also, in the publication of JP-A No. 3-106833, there is a description of a method of producing a 4,4'-dialkylbiphenyl continuously, the method comprising a step of reacting biphenyls including biphenyl and monoalkylbiphenyls with an olefin or the like in the presence of an acid catalyst, a separating step of separating only a 4,4'-dialkylbiphenyl and a circulation step of returning the remainder product from which the 4,4'-dialkylbiphenyl has been separated. However, there is no disclosure of a method of producing dialkylbiphenyls and trialkylbiphenyls, which are the compounds intended in the present invention except for 4,4'-dialkylbiphenyl. Also, there is a fear that if biphenyl having a melting point as high as 70° C. exists in a high concentration, it is solidified in the circulation step. However, these problems and a method of running a continuous operation stably nowhere are disclosed. Also, 4,4'-dialkylbiphenyl has a melting point as high as 65° C., so that there is a fear that it precipitates as a crystal when cooled if it exists in a high concentration in dialkylbiphenyls. It is therefore preferable that the ratio of 4,4'-dialkylbiphenyl is small when polyalkylbiphenyls such as dialkylbiphenyls and trialkylbiphenyls are used for a pressure-sensitive paper solvent and the like.

SUMMARY OF THE INVENTION

It is an object of the present invention to provide a method of producing dialkylbiphenyls and trialkylbiphenyls primarily with high efficiency in a continuous flow system.

The inventors of the present invention have made earnest studies to solve the above problem, leading to the completion of the invention. According to a first aspect of the present invention, there is provided a method of continuously producing polyalkylbiphenyls, the method comprising (1) a step of supplying a reaction raw material containing at least biphenyl and an olefin to a fixed-bed flow system reactor wherein the ratio of olefin/biphenyl is 0.3 to 3 (mol ratio) at the inlet of the reactor and reacting the raw material in the presence of a solid acid catalyst to obtain a reaction mixture containing monoalkylbiphenyls and dialkylbiphenyls, (2) a step of separating a fraction containing biphenyl and at least a part of monoalkylbiphenyls from the above reaction mixture, (3) a step of circulating the fraction separated in the step (2) to the reactor such that the ratio by weight of biphenyl to monoalkylbiphenyls is made to be 0.1 or more and is made to be less than the solubility of biphenyl to monoalkylbiphenyls at a circulation temperature and (4) a step of recovering polyalkylbiphenyls containing at least one of 3,3-dialkylbiphenyl, 3,4'-dialkylbiphenyl, 4,4'-dialkylbiphenyl and 3,5'-dialkylbiphenyl from the reaction mixture through the step (2).

According to a second aspect of the present invention, there is provided a method of continuously producing polyalkylbiphenyls, wherein the concentration of dialkylbiphenyls in the fraction separated in the step (2) is preferably made to be 15% by mass or less.

According to a third aspect of the present invention, there is provided a method of continuously producing polyalkylbiphenyls, wherein the amount of dialkylbiphenyls in the fraction separated in the step (2) is preferably made to be 30% by mass or less of the amount of dialkylbiphenyls generated in the step (1).

DESCRIPTION OF THE PREFERRED EMBODIMENT

Figure 1:
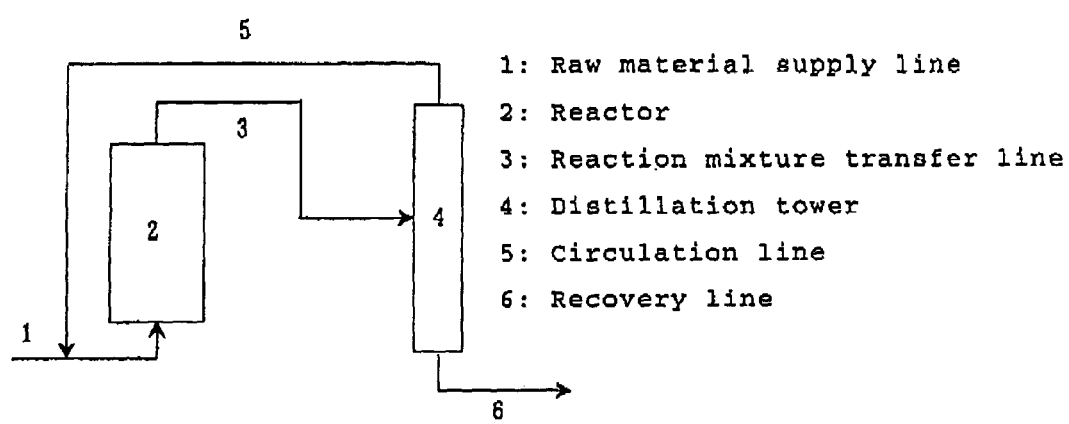
FIG. 1 is a view showing one embodiment of a method according to the present invention.

The details of each step will be explained hereinbelow.

<Step (1): Reaction Step>

In this step, biphenyl and an olefin are supplied as major raw materials to a fixed-bed flow system reactor filled with a solid acid catalyst to produce polyalkylbiphenyls primarily containing dialkylbiphenyls, trialkylbiphenyls and the like continuously through the alkylation of the biphenyl and the trans-alkylation and isomerization of the alkylbiphenyl.

Typical examples of dialkylbiphenyls include 3,3'-dialkylbiphenyl, 3,4-dialkylbiphenyl, 4,4'-dialkylbiphenyl and 3,5-dialkylbiphenyl. However, 4,4'-dialkylbiphenyl has a high-melting point therefore there is a fear that it precipitates as a crystal when cooled. Also, a dialkylbiphenyl having an o-position substituent has a low-boiling point. Therefore, the inclusion of 4,4'-dialkylbiphenyl or dialkylbiphenyls having an o-position substituent is undesirable when using dialkylbiphenyls or trialkylbiphenyls as a pressure-sensitive paper solvent.

As the solid acid catalyst, any material which can be used in a fixed-bed flow reaction system may be used without any particular limitation, and activated clay, silica alumina, zeolite, solid phosphoric acid, ion exchange resins and the like may be used. Among these catalyst materials, silica alumina is particularly preferable from the viewpoint of decreasing the production of 4,4'-dialkylbiphenyl and dialkylbiphenyls having an o-position substituent, producing 3,3'-dialkylbiphenyl, 3,4'-dialkylbiphenyl and 3,5-dialkylbiphenyl primarily, having high catalyst activity and a long catalyst life, decreasing the generation of byproducts and being relatively inexpensive catalyst coat.

As the olefin, though any olefin can be used, those having 2 to 6 carbon atoms are preferable. Specific examples of the olefin include ethylene, propylene, 1-butene, 2-butene, isobutene, 1-pentene, 2-pentene, 3-methyl-1-butene, 2-methyl-1-butene, 2-methyl-2-butene, 1-hexene, 2-hexene, 3-hexene, 2-methyl-1-pentene, 4-methyl-1-pentene, 2-methyl-2-pentene, 4-methyl-2-pentene, 3-methyl-1-pentene, 3-methyl-2-pentene, 2,3-dimethyl-1-butene, 3,3-dimethyl-1-butene, 2,3-dimethyl-2-butene and 2-ethyl-1-butene. Among these compounds, propylene, 1-butene, 2-butene and isobutene are particularly preferable. Plural olefins may be used in combinations.

In this step, besides the biphenyl and the olefin, low-boiling point fractions recovered in a separation step which will be explained later, that is, biphenyl, monoalkylbiphenyls, dialkylbiphenyls having an o-position substituent and the like are utilized as reaction raw materials.

Reaction temperature is preferably 100 to 300° C. and in the case of intending to primarily produce dialkylbiphenyls excluding a 4,4'-dialkylbiphenyl, a temperature range from 160° C. to 270° C. is preferable. When the temperature is less than 100° C., the alkylation proceeds unsatisfactorily, whereas when the temperature exceeds 300° C., decomposition/coloration, a reduction in yield, life shortening of the catalyst and the like are caused. Therefore, the temperature out of the above defined range is undesirable. When, particularly, the temperature is 160 to 270° C., the obtained composition becomes to be close to its thermodynamic equilibrium composition. Therefore, the production of dialkylbiphenyls having an opposition substituent and 4,4'-dialkylbiphenyl is suppressed and 3,3'-dialkylbiphenyl, 3,4'-dialkylbiphenyl and 3,5-dialkylbiphenyl are mainly obtained.

Reaction pressure is preferably normal pressure to 5.0 MPa in view of production efficiency though any pressure can be used. Liquid space velocity (LHSV) is preferably 0.1 $hr^{-1}$ to 3.0 $hr^{-1}$ and more preferably 0.3 $hr^{-1}$ to 1.5 $hr^{-1}$, the LHSV range exceeding 3.0 $hr^{-1}$ is undesirable because the production amount of dialkylbiphenyls having an o-position substituent is increased.

The mol ratio of olefin/biphenyl at the inlet of the reactor is preferably 0.3 to 3 and more preferably 0.5 to 1.5. When the mol ratio is less than 0.3, biphenyl cannot be circulated in a circulation step which will be explained later. In order to circulate biphenyl which is a solid at an ambient temperature, it is necessary to circulate enough amount of monoalkybiphenyls in which biphenyl is to be dissolved in such a way that the ration of biphenyl to monoalkylbiphenyls in circulation is less than the solubility of it to them. When the ratio of the olefin to biphenyl is small, a required amount of monoalkybiphenyls cannot be secured. Also, when the mol ratio of olefin/biphenyl exceeds 3, the amount of trialkylbiphenyls to be produced is increased, but, on the other hand, the amount of heavy byproducts and light byproducts such as olefin oligomers is increased, consequently production efficiency is decreased and deterioration in the activity of the catalyst is accelerated. Therefore, a ratio out of the above defined range is undesirable. Also, when the ratio of the olefin to the biphenyl is within the above range, the olefin supplied is consumed by the reaction. On the other hand, when the ratio exceeds the above range, it is necessary to discharge an unreacted olefin from the reactor. In this case, it is necessary to install a vapor-liquid separator and the like in the separation step, which is undesirable from the viewpoint of the production cost of equipment.

In this step, a reaction mixture containing light byproducts comprising an olefin oligomer, unreacted biphenyl, biphenyl produced resulting from the trans-alkylation or isomerization of the alkylbiphenyl, a monoalkylbiphenyl. dialkylbiphenyl and a trialkylbiphenyl which are major target products and besides, heavy products such as a tetraalkylbiphenyl is obtained. As dialkylbiphenyls, 3,3'-dialkylbiphenyl, 3,4-dialkylbiphenyl, 4,4'-dialkylbiphenyl and 3,5-dialkylbiphenyl are included and in addition, dialkylbiphenyls having an o-position substituent and the like are also included. As trialkylbiphenyls, a 3,5,3'-trialkylbiphenyl and 3,5,4'-trialkylbiphenyl are included.

<Step (2): Separation Step>

In this step, a fraction containing biphenyl and monoalkylbiphenyls, and a fraction containing dialkylbiphenyls and trialkylbiphenyls which are main target products as polyalkylbiphenyls are separated respectively by distillation from the reaction mixture obtained in the reaction step to recover each fraction. Light byproducts and heavy byproducts are separated and removed, if necessary. Among dialkylbiphenyls, those having an opposition substituent are recovered together with the biphenyl and monoalkylbiphenyls because their boiling points are close to that of p-monoalkylbiphenyls.

In this step, there is no particular limitation to a distillation method and the number of distillation towers insofar as biphenyl including unreacted biphenyl and monoalkylbiphenyls are separated simultaneously and the decomposition of polyalkylbiphenyls such as dialkylbiphenyls and trialkylbiphenyls does not proceed. As shown in FIG. 1, for example, biphenyl, monoalkylbiphenyls and light byproducts can be recovered from the top of a distillation tower (4) and dialkylbiphenyls, trialkylbiphenyls and heavy products can be recovered from the bottom of the distillation tower (4) through a line 6. Alternatively, biphenyl, monoalkylbiphenyls and light byproducts maybe recovered from the top of the distillation tower (4), dialkylbiphenyls and trialkylbiphenyls may be recovered from a middle position of the distillation tower (4) and heavy byproducts may be recovered from the bottom of the distillation tower (4). Also, a method may be adopted in which light byproducts are recovered from the top of the distillation tower (4), biphenyl and monoalkylbiphenyls are recovered from the middle position of the distillation tower (4) and dialkylbiphenyls, trialkylbiphenyls and heavy byproducts are recovered from the bottom of the distillation tower (4). Also, a part of monoalkylbiphenyls may be recovered together with or separately from a dialkyklbiphenyl and trialkylbiphenyls as a product.

Although distillation temperature and pressure are properly selected according to a distillation method, the operation is generally carried out at a temperature ranging from 100 to 300° C. under a pressure ranging from 2 to 700 kPa. When a large amount of light byproducts is obtained, another distillation tower may be provided just after the reaction stop to remove these by products. However, under the reaction condition that these light byproducts are not almost produced, such a distillation tower is not necessarily needed.

There is the case where dialkylbiphenyls gets mixed in the fraction containing biphenyl and monoalkylbiphenyls to be separated depending on distillation conditions. Dialkylbiphenyls to be mixed includes a small amount of high-boiling point 4,4'-dialkylbiphenyls and mainly those having lower boiling points than 4,4'-dialkylbiphenyls. In the case where a part of dialkylbiphenyls are separated together with biphenyl and monoalkylbiphenyls and circulated to the reactor in a circulation step which will be explained later, the yield of dialkylbiphenyls decreases and the amount of 4,4-dialkylbiphenyls contained in the product increases. In the case of intending to primarily produce dialkylbiphenyls excluding 4,4'-dialkylbiphenyls, the content of dialkylbiphenyls in the fraction containing biphenyl and monoalkylbiphenyls to be separated in the step (2) is made to be preferably 15% by mass or less and more preferably 10% by mass or less. Also, the amount of dialkylbiphenyls contained in the fraction containing biphenyl and monoalkylbiphenyls to be separated in the step (2) is made to be preferably 30% by mass or less and more preferably 20% by mass or less based on the amount of dialkylbiphenyls produced in the reaction step (1).

<Step (3): Circulation Step>

In this step, the fraction containing biphenyl and monoalkylbiphenyls separated in the separation step (2) is circulated to the reactor.

The amount of biphenyl in the fraction circulated in this step is designed such that the ratio by weight of biphenyl/monoalkylbiphenyls is 0.1 or more and is less than the volubility of biphenyl to monoalkylbiphenyls at the temperature of the circulation flow. When such fraction is separated in the separation step (2), it can be circulated without adjustments in this step. When monoalkylbiphenyls are not present in an amount enough to be able to dissolve at the point of the lowest temperature in the circulation line, there is a fear that biphenyl crystallizes out at that point, so that it cannot be circulated. Also, when the excessive ratio of biphenyl to monoalkylbiphenyls is undesirable because of decreased productivity.

Though an aforementioned, dialkylbiphenyls having an o-substituent are recovered together with biphenyl and monoalkylbiphenyls simultaneously, those are circulated to the reactor and then can be isomerized and converted into the target product. In the case that dialkylbiphenyls and the like are included in the circulated fraction, even if the amount of biphenyl in that fraction is more than the solubility of biphenyl to monoalkylbiphenyls, biphenyl may not precipitate. However, it is preferable that the amount of biphenyl in the circulated fraction is controlled so as to be less than the solubility of biphenyl to monoalkylbiphenyls, in order to perform the circulation step safety and stably.

The above ratio limitations in circulation maybe easily achieved by controlling the reaction conditions at the reaction step (1) and the distillation conditions at the separation step (2).

In the meantime, it is undesirable to make the separated byproducts heavier than the target product circulate circulated together in the circulation step because it causes a reduction in catalyst life and productivity at the same time.

It is to be noted that according to the production method of the present invention, it is unnecessary to use any other solvents in order to circulate biphenyl at a steady state of operation step; however, solvents may be used at the start of the operation. As the solvent thus used, polyalkylbenzenes having a plurality of alkyl groups are preferable. Among these polyalkylbenzenes, those provided with an alkyl group having 1 to 3 carbon atoms are preferable and those provided with an alkyl group having 1 to 2 carbon atoms are more preferable. Particularly preferable and specific examples include xylene, trimethylbenzene, diethylbenzene and triethylbenzene. Monoalkylbiphenyls may also be used as a solvent for filling the equipment at start to prevent supplied biphenyl from crystallizing. Alicyclic hydrocarbons such as cyclohexane may also be used. These solvents may be used by mixture. Even in the case of using a solvent at the start of the operation, as the operation becomes closer to the steady state, the solvent is gradually eliminated from the system due to, for example, the loss of the solvent in the aforementioned separation step and at last there is in usual no solvent existing in the system. The operation may be however run without any problem in such a state as some solvent are present in the system.

<Step (4): Recovery Step>

This is a step of recovering polyalkylbiphenyls containing at least one of 3,3'-dialkylbiphenyls, 3,4'-dialkylbiphenyls, 4,4'-dialkylbiphenyls and 3,5-dialkylbiphenyls from the reaction mixture from which the fraction containing at least a part of biphenyl and moncalkylbiphenyls has been separated in the separation step (2). This recovery may be made by distillation. This step may be carried out simultaneously with the separation step (2) or separately after the separation step (2).

The resulting polyalkylbiphenyls may be refined by distillation into a desired composition. Also, dialkylbiphenyls or trialkylbiphenyls can be mainly isolated as a single component. When monoalkylbiphenyls are contained, they may be isolated. Moreover, it is possible to separate only a specific isomer. Polyalkylbiphenyls obtained as a product in this manner are used in applications such as a pressure-sensitive paper solvent, heating medium, insulating oil and various kinds of solvents. In the case of applications having the possibility of being stored at lower temperatures, the content of 4,4'-dialkylbiphenyls which have a higher melting point and tend to crystallize out at low temperatures is preferably small.

According to the present invention, biphenyl and an olefin are used as starting materials and a fraction containing biphenyl and monoalkylbiphenyls is separated from the reaction mixture and used as a reaction raw material through circulation step, whereby polyalkylenebiphenyls such as dialkylbiphenyls and trialkylbiphenyls can be efficiently produced in a high yield. The fraction containing biphenyl and monoalkylbiphenyls separated from the reaction mixture is circulated to a reaction step (2) under the condition that biphenyl is dissolved in monoalkylbiphenyls and dose not crystallize out at any point in the circulation. This ensures that it is unnecessary to use any other solvent for solving biphenyl and it is also unnecessary to provide the whole circulation line with heat insulation arrangement, making it possible to simplify production equipment and to decrease production costs. It is thus possible to provide a very efficient method for producing polyalkylbiphenyls.

EXAMPLES

Example 1

(Continuous Production)

An operation was carried out using the equipment shown in FIG. 1. A fixed bed continuous flow type cylindrical reactor 2 having a diameter of 8 mm and a height of 280 mm was filled with 7 g of a silica alumina catalyst. Biphenyl and propylene were supplied continuously to the reactor 2 through a raw material supply line 1. The reaction mixture was fed continuously to a distillation tower 4 through a transfer line 3. Biphenyl, monoalkylbiphenyls and the like were recovered from the tower top and returned to the reactor 2 through a circulation line 5 and also a target product was recovered from the tower bottom through a recovery line 6. At the start of the reaction, monoisopropylbiphenyls were filled in the system in advance to prevent biphenyl from being solidified until the system was stabilized.

In the reactor 2, the following reaction condition was adopted: reaction temperature: 220° C., reaction pressure: 0.9 MPa, propylene/biphenyl (mol ratio) at the inlet of the reactor: 0.6 and liquid flow velocity LHSV=1.0. The results of the analysis of the liquid composition at the inlet and outlet of the reactor are shown in Table 1.

TABLE 1

| | Reactor inlet | Reactor outlet |
|---|---|---|
| Light content | 2.0% | 1.9% |
| Biphenyl | 40.3% | 26.6% |
| Monoisapropylbiphenyl | 48.9% | 44.5% |
| Light diisopropylbiphenyl | 2.3% | 2.4% |
| Target diisopropylbiphenyl | 6.3% | 20.6% |
| Triisopropylbiphenyl | 0.0% | 3.0% |
| Heavy content | 0.0% | 1.2% |

The ratio of isomers in monoisopropylbiphenyls contained in the reaction mixture at the outlet of the reactor are shown in Table 2.

TABLE 2

| | Ratio of isomers in monoisopropylbiphenyl |
|---|---|
| Ortho-monoisopropylbiphenyl | 1.6% |
| Metha-monoisopropylbiphenyl | 61.6% |
| Para-monoisopropylbiphenyl | 36.8% |

The condition of the distillation tower 4 were as follows: number of theoretical stages: 80, pressure: 150 mmHg (20 kpa), tower top temperature. 210° C. and tower bottom temperature: 270° C. A fraction containing biphenyl and monoisopropylbiphenyl (tower top recovery solution) was recovered from the tower top and a fraction containing diisopropylbiphenyl, triisopropylbiphenyl and a heavy content (tower bottom recovery solution) was recovered from the tower bottom. The results of the analysis of each fraction (recovery solution) are shown in Table 3.

TABLE 3

| | Tower top recovery solution | Tower bottom recovery solution |
|---|---|---|
| Recovery rate | 81% | 19% |
| Light content | 2.7% | 0.0% |
| Biphenyl | 35.7% | 0.0% |
| Monoisopropylbiphenyl | 51.7% | 0.0% |
| Light diisopropylbiphenyl | 2.3% | 0.1% |
| Target diisopropylbiphenyl | 5.3% | 84.9% |
| (4,4'-diisopropylbiphenyl) | (0.0%) | (14.1%) |
| Triisopropylbiphenyl | 0.0% | 11.5% |
| Heavy content | 0.0% | 3.6% |

The ratio by weight of biphenyl/monoisopropylbiphenyl in the fraction recovery from the tower top was 0.69 and the precipitation of crystals in the circulation line was not seen. The liquid temperature in the circulation line was 35° C. Also, the content of diisopropylbiphenyl in the fraction recovery from the tower top was 7.6% by mass and this amount was 27.6% by mass of the amount of diisopropylbiphenyl measured at the inlet of the reactor. As a result, the amount of 4,4'-diisopropylbiphenyl in diisopropylbiphenyl contained in the fraction recovery from the tower bottom was 14.1% by mass.

The fraction recovery from the tower bottom was distilled and separated into diisopropylbiphenyl, triisopropylbiphenyl and heavy byproducts.

As the result of this series of operations, 3670 g of diisopropylbiphenyl, 200 g of triisopropylbiphenyl and 200 g of the heavy product were obtained from 1560 g of propylene and 2600 g of biphenyl. Diisopropylbiphenyl and triisopropylbiphenyl were obtained at a yield as high as 93%. In the resulting diisopropylbiphenyl, the amount of 3,3'-diisopropylbiphenyl was 26.9% by mass, the amount of 3,4'-diisopropylbiphenyl was 42.4% by mass, the amount of 4,4'-diisopropylbiphenyl was 14.6% by mass and the amount of 3,5-diisopropylbiphenyl was 4.8% by mass.

(Confirmation of the Solubility of Biphenyl in Monoisopropylbiphenyl)

In order to confirm the condition of the precipitation of biphenyl crystals in the circulation line, the solubility of biphenyl to monoisopropylbiphenyl was measured. The results are shown in Table 4. This results shows that biphenyl crystals can not precipitate in the above circulation line kept at 35° C. because of much amount of monoisopropylbiphenyl. However, if the amount of monoisopropylbiphenyl becomes small, the possibility that biphenyl will precipitate will increase.

TABLE 4

| Temperature | Biphenyl/monoisopropylbiphenyl |
|---|---|
| 10° C. | 0.35 |
| 28° C. | 0.58 |
| 35° C. | 0.89 |
| 50° C. | 1.99 |

(Confirmation of Precipitation of 4,4'-diisopropylbiphenyl Crystals)

Solutions each containing 4,4'-diisopropylbiphenyl in ratios of 15% by mass and 30% by mass in diisopropylbiphenyl were respectively prepared in an amount of 50 g. Each solution was cooled to −10° C. As a result, a large amount of 4,4'-diisopropylbiphenyl precipitated in the case of the solution containing 30% by mass of 4.4'-diisopropylbiphenyl and no precipitation of crystals was observed in the case of the solution containing 15% by mass of 4,4'-diisopropylbiphenyl. Therefore, as mentioned above, in the case where the content of diisopropylbiphenyl contained in the solution recovery from the tower top of the distillation tower is 7.6% by mass and this amount is 27.6% by mass of the amount of diisopropylbiphenyl measured at the outlet of the reactor, with the result that the amount of 4,4'-diisopropylbiphenyl in diisopropylbiphenyl as a product is 14.1% by mass, there is no particular problem as to the low-temperature characteristics of the product. However, if the amount of diisopropylbiphenyl contained in the solution recovery from the tower top of the distillation tower becomes increase and the amount of 4,4'-diisopropylbiphenyl in diisopropylbiphenyl as a product becomes increase, the low-temperature characteristics will deteriorate.

Comparative Example 1

The same procedures as in Example 1 were carried out except that the mol ratio of propylene/biphenyl at the inlet of the reactor was changed to 0.15. However, as monoisopropylbiphenyl filled in the system before the start of the reaction was reacted with propylene and discharged out of the system, the concentration of biphenyl in the circulation line increased and the solution in the circulation line coagulated, so that the reaction could not be continued. The content in the circulation line was taken out and heated to melt the coagulated content, which was then analyzed, to find that the concentration of biphenyl was 55% by mass (biphenyl/monoisopropylbiphenyl=1.29).

Example 2

The same procedures as in Example 1 were carried out except that the operation temperature of the distillation tower was changed such that the temperature of the tower top was 195° C. and the temperature of the tower bottom was 265° C. The value of analysis of each solution recovery from the tower top and the tower bottom is shown in Table 5. The results shows that the larger amount of diisopropylbiphenyl is circulated, the higher becomes the concentration of 4,4'-diisopropylbiphenyl in diisopropylbiphenyl in the recovery line and the larger amount of heavy components is produced due to increase of the concentration of diisopropylbiphenyl in the reactor.

TABLE 5

|  | Tower top recovery solution | Tower bottom recovery solution |
| --- | --- | --- |
| Recovery rate | 85% | 15% |
| Light content | 5.1% | 0.0% |
| Biphenyl | 33.8% | 0.0% |
| Monoisopropylbiphenyl | 45.1% | 0.0% |
| Light diisopropylbiphenyl | 4.9% | 0.1% |
| Target diisopropylbiphenyl | 11.1% | 57.4% |
| (4,4'-diisopropylbiphenyl) | (0.8%) | (24.2%) |
| Triisopropylbiphenyl | 0.0% | 29.7% |
| Heavy content | 0.0% | 12.8% |

Comparative Example 2

The same procedures as in Example 1 were carried out except that the mol ratio of propylene/biphenyl at the inlet of the reactor was changed to 4. The results of analysis of each liquid composition of the tower top and bottom recover liquids 72 hours after the reaction was started are shown in table 6. A larger amount of heavy constituents were produced, showing that the raw material could be inefficiently converted into diisopropylbiphenyls. Also, a large amount of propylene oligomers were produced and a reduction in catalyst life was observed. Moreover, a lot of propylene was unreacted and it was therefore necessary to install a vapor-liquid separator in the upstream side of the distillation tower.

TABLE 6

|  | Tower top recovery solution | Tower bottom recovery solution |
| --- | --- | --- |
| Recovery rate | 17% | 83% |
| Light content | 16.9% | 0.0% |
| Biphenyl | 15.8% | 0.0% |
| Monoisopropylbiphenyl | 44.8% | 0.0% |
| Light diisopropylbiphenyl | 8.4% | 0.0% |
| Target diisopropylbiphenyl | 14.1% | 33.9% |
| (4,4'-diisopropylbiphenyl) | (0.0%) | (6.5%) |
| Triisopropylbiphenyl | 0.0% | 44.6% |
| Heavy content | 0.0% | 21.5% |

What is claimed is:

1. A method of continuously producing polyalkylbiphenyls, comprising the steps of:
   (1) supplying reaction raw materials containing at least biphenyl, dialkylbiphenyl and an olefin to a fixed-bed flow system reactor wherein the mol ratio of olefin/biphenyl is 0.3 to 3 at the inlet of the reactor and reacting the raw materials in the presence of a solid acid catalyst to obtain a reaction mixture containing monoalkylbiphenyls and dialkylbiphenyls;
   (2) separating a fraction containing biphenyl and at least a part of monoalkylbiphenyls from said reaction mixture, wherein the concentration of dialkylbiphenyls in the fraction separated in said step (2) is made to be 15% by mass or less and the amount of dialkylbiphenyls in the fraction separated in said step (2) is made to be 30% by mass or less of the amount of dialkylbiphenyls produced in said step (1);
   (3) circulating the fraction separated in said step (2) to said reactor such that the ratio by weight of biphenyl to monoalkylbiphenyls is designed to be 0.1 or more and is designed to be less than the soluability of biphenyl to monoalkylbiphenyl at a circulation temperature; and
   (4) recovering polyalkylbiphenyls containing at least one of 3,3'-dialkylbiphenyl, 3,4'-dialkylbiphenyl, 4,4'-dialkylbiphenyl and 3,5'-dialkylbiphenyl from the reaction mixture through said step (2), whereby no precipitation of 4,4'-dialkylbiphenyl crystal is observed at −10° C.

2. A method of continuously producing polyalkylbiphenyls according to claim 1, wherein the olefin has 2 to 6 carbon atoms.

3. A method of continuously producing polyalkylbiphenyls according to claim 2, wherein the dialkylbiphenyl reaction raw material is a 3,3'-, 3,4'- , 4,4'- or 3,5-dialkylbiphenyl, the olefin is propylene, 1-butene, 2-butene or isobutene and the acid catalyst is silica alumina, arid wherein the mol ratio of olefin/biphenyl is 0.5–1.5 at the inlet of the reactor.

4. A method of continuously producing polyalkylbiphenyls according to claim 3, wherein the fraction separated in step 2 contains up to 10 mass percent of dialkylbiphenyl and is made to be 20 mass percent or less of the amount of dialkylbiphenyls produced in said step (1).

* * * * *